United States Patent
Pitaru et al.

(10) Patent No.: US 12,115,196 B1
(45) Date of Patent: Oct. 15, 2024

(54) METHODS FOR TREATING NEUROLOGICAL DISEASES

(71) Applicant: Cytora Ltd., Ramat Gan (IL)

(72) Inventors: Sandu Pitaru, Tel Aviv (IL); Haim Goltsman, Gesher Haziv (IL); Belly Koren, Shchenia (IL); Avital Amilov, Kiriat Bialik (IL)

(73) Assignee: CYTORA LTD., Ramat Gan (IL)

( * ) Notice: Subject to any disclaimer, the term of this patent is extended or adjusted under 35 U.S.C. 154(b) by 0 days.

(21) Appl. No.: 18/474,676

(22) Filed: Sep. 26, 2023

(51) Int. Cl.
*A61K 35/38* (2015.01)
*A61K 9/00* (2006.01)
*A61M 5/32* (2006.01)

(52) U.S. Cl.
CPC ............ *A61K 35/38* (2013.01); *A61K 9/0019* (2013.01); *A61M 5/32* (2013.01)

(58) Field of Classification Search
CPC ....... A61K 35/38; A61K 9/0019; A61M 5/32; A61M 2205/3334; A61M 2202/0464; A61M 2210/1003; A61B 2010/007; A61B 2018/0044
See application file for complete search history.

(56) References Cited

U.S. PATENT DOCUMENTS

| | | | | |
|---|---|---|---|---|
| 2010/0226896 A1* | 9/2010 | Dracker | ............... | A61K 35/545 424/93.7 |
| 2012/0087869 A1* | 4/2012 | Thakker | ............... | A61K 31/711 424/9.34 |
| 2019/0159804 A1* | 5/2019 | Cameron | ............ | A61M 5/3286 |

FOREIGN PATENT DOCUMENTS

| WO | 2008132722 A1 | 11/2008 |
|---|---|---|
| WO | 2019016799 A1 | 1/2019 |

OTHER PUBLICATIONS

Lee et al., (2008) Cyclooxygenase polymorphisms and risk of cardiovascular events: the Atherosclerosis Risk in Communities (ARIC) study. Clin Pharmacol Ther Clin Pharmacol Ther. Author manuscript; available in PMC Feb. 15, 2008. Published in final edited form as: Clin Pharmacol Ther. Jan. 2008; 83(1): 52-60.

Lee et al., (2012) A randomized trial of mesenchymal stem cells in multiple system atrophy. Ann Neurol 72(1): 32-40.

Singer et al., (2019) Intrathecal administration of autologous mesenchymal stem cells in multiple system atrophy. Neurology 93(1): e77-e87.

* cited by examiner

*Primary Examiner* — Amber R Stiles
(74) *Attorney, Agent, or Firm* — BROWDY AND NEIMARK, PLLC

(57) ABSTRACT

The present invention provides methods of treating neurological diseases and disorders by intrathecal administration of cells, such as human stem cells, while the method provides a reduced rate of side effects associated with intrathecal administration.

17 Claims, No Drawings

METHODS FOR TREATING NEUROLOGICAL DISEASES

FIELD OF THE INVENTION

The present invention is related to methods of administering human therapeutic cells for the treatment of neurodegenerative diseases or disorders thereof.

BACKGROUND OF THE INVENTION

Intrathecal (IT) administration is a well-known medical procedure whereby medication is delivered to the central nervous system. These medications include drugs, biologicals and therapeutic cells that are capable of releasing neurotrophic factors aiming at treating neurological diseases or disorders. IT delivery of therapeutic cells for the treatment of neurodegenerative diseases including Multiple System Atrophy (MSA) has been associated with adverse events, e.g., back pain, referral lower limb pain and thickening of the nerve roots in the proximity of the IT site of injection as disclosed by Magnetic Resonance Imaging (MRI) abnormalities (Singer et al. Neurology, 2019). The intensity and duration of these adverse events increased with dosage augmentation thereby limiting the therapeutic dose. The MRI analysis suggested that following the IT administration a significant number of cells remained clumped in the lumbar area of the spinal cord and cauda equina, at a considerable distance from the brain, a fact that might reduce the efficacy of this treatment. Alternative procedures for delivering cells to the central nervous is by intra-carotid delivery. However, this approach is associated with mini-ischemic strokes due to small artery blockage by cell clumps. (Lee et al., Clinical Pharmacology and Therapeutics, 2008; Lee et al., Annals of Neurology, 2012).

Thus, there is still a need in the art to develop a safe and effective method of IT administration procedure that is capable of administering high doses of cells with therapeutic efficacy for the treatment of neurodegenerative diseases while minimizing the side effects associated with the IT administration procedure

SUMMARY OF THE INVENTION

The present invention provides a method of treating a neurological disease or disorder by intrathecally administering a therapeutic cell suspension to a patient in need thereof, while overcoming previously reported side effects associated with intrathecal administration. According to one aspect, the present invention provides a method for treating a neurological disease or disorder in a subject in need thereof comprising the steps of:
  (i) performing a lumbar puncture; and
  (ii) intrathecally administering from 5 to 40 ml of a therapeutic cell suspension at a rate of from 0.1 to 2 ml/min,
wherein the amount of the administered cells is from $1\times10^6$ to $1\times10^9$ and/or the therapeutic cell suspension comprises from $0.1\times10^5$ to $5\times10^7$ cells/ml. In some examples, the rate of administering is from 0.1 to 1.5 ml/min or from 0.5 to 1.5 ml/min. In some examples, the amount of the administered cells is from $1\times10^6$ to $5\times10^8$. In some examples, the method comprises intrathecally administering from 5 to 35 ml of the therapeutic cell suspension. In some examples, the method comprises intrathecally administering from 5 to 30 ml of the therapeutic cell suspension. In some examples, the method comprises intrathecally administering from 5 to 25 ml of the therapeutic cell suspension. In some examples, the therapeutic cell suspension comprises from $0.5\times10^5$ to $5\times10^7$ cells/ml. In some examples, the therapeutic cell suspension comprises from $0.5\times10^6$ to $5\times10^7$ cells/ml. In other examples, the method further comprises drawing a volume from 5 to 40 ml of cerebrospinal fluid (CSF) at step (i) and wherein the volume of the administered therapeutic cell suspension is equal to or up to ±5 ml of the volume of CSF drawn in step (i). In some examples, the method comprises drawing a volume from 5 to 35 ml of cerebrospinal fluid (CSF) at step (i). In some examples, the method comprises drawing a volume from 5 to 30 ml of cerebrospinal fluid (CSF) at step (i). In some examples, the method comprises drawing a volume from 5 to 25 ml of cerebrospinal fluid (CSF) at step (i). Thus, in some examples, the present invention provides a method for treating a neurological disease or disorder in a subject in need thereof comprising the steps of:
  (i) performing a lumbar puncture and drawing a volume from 5 to 25 ml of cerebrospinal fluid (CSF); and
  (ii) intrathecally administering a therapeutic cell suspension at a rate of from 0.1 to 1.5 ml/min,
wherein the volume of the administered therapeutic cell suspension is equal to or up to ±5 ml the volume of CSF drawn in step (i). According to some examples, the amount of the administered cells is from $1\times10^6$ to $5\times10^8$. According to some examples, the therapeutic cell suspension comprises from $1\times10^6$ to $2\times10^7$ cells/ml. According to some examples, the therapeutic cell suspension comprises from $1\times10^5$ to $2\times10^7$ cells/ml. In some examples drawing CSF and administering the therapeutic cell suspension is performed simultaneously.

According to one example, the neurological disease or disorder is a neurodegenerative disease. According to some examples, the neurodegenerative disease is selected from the group comprising of: Multiple System Atrophy, Alzheimer's Disease, Pick Disease, Parkinsonism, Idiopathic Parkinson's Disease, Progressive Supranuclear Palsy, Corticobasal Degeneration, Striatonigral Degeneration, Shy-Drager Syndrome, Olivopontocerebellar Atrophy, Huntington Disease, Spinocerebellar Ataxias, Friedreich Ataxia, Ataxia-Telangiectasia, Amyotrophic Lateral Sclerosis, Bulbospinal Atrophy, Spinal Muscular Atrophy, and combinations thereof. According to a more specific example, the neurodegenerative disease is multiple system atrophy. According to some embodiments, the neurological disease or disorder is selected from the group comprising of a trauma to the central nervous system (CNS), brain trauma, trauma to the spinal cord, trauma to the spinal ganglions, and a chronic disease affecting the central nervous system. Non-limiting examples for such diseases are diabetes, lupus, post-atherosclerotic stroke and post-hemorrhagic stroke caused by intervertebral disc pathologies.

According to another aspect, the present invention provides a method for intrathecally administering a therapeutic cell suspension to a subject in need thereof comprising the steps of:
  (i) performing a lumbar puncture using a spinal needle and drawing a volume of from 5 to 40 ml of cerebrospinal fluid (CSF); and
  (ii) intrathecally administering a therapeutic cell suspension at a rate of from 0.1 to 1.5 ml/min
wherein the volume of the administered therapeutic cell suspension is equal to or about ±5 ml the volume of CSF drawn in step (i). According to some examples, the amount of the administered cells is from $1\times10^6$ to $1\times10^9$. According to some examples, the therapeutic cell suspension comprises from $1\times10^5$ to $5\times10^7$ cells/ml. According to some examples, the therapeutic cell suspension comprises from $1\times10^6$ to $5\times10^7$ cells/ml.

According to any one of the above aspects and examples, the rate of administration of the therapeutic cell suspension in step (ii) is from 0.5 to 1.5 ml/min.

According to any one of the above aspects and examples, the method comprises administering from $1\times10^7$ to $1\times10^8$ cells.

According to any one of the above aspects and examples, the volume of the therapeutic cell suspension administered in step (ii) equals to the volume of CSF drawn in step (i).

According to any one of the above aspects and examples, the concentration of cells in the therapeutic cell suspension is from $0.5\times10^6$ to $5\times10^7$ cells/ml, $1\times10^6$ to $5\times10^7$ cells/ml, from $1\times10^6$ to $4\times10^7$ cells/ml, from $1\times10^6$ to $2\times10^7$ cells/ml or from $1\times10^6$ to $10\times10^6$ cells/ml.

According to any one of the above aspects and examples, the therapeutic cell suspension is administered via the spinal needle. According to any one of the above aspects and examples, the CSF is drawn via the spinal needle. According to a more specific example, the therapeutic cell suspension is mixed during administration to prevent the clumping of cells. According to some embodiments, cell clumping comprises cell clumping adjacent to the injection site. According to some embodiments, cell clumping comprises cell clumping adjacent to the nerve roots of the cauda equina near the injection site. According to yet another example, the mixing comprises rotating or tilting the device comprising the therapeutic cell suspension manually or by a designated automatic device.

According to any one of the above aspects and examples, the method is characterized by a lower rate of side effects associated with intrathecal administration of cells in comparison to a corresponding method comprising intrathecal administering cells at a rate higher than 2 ml/min. According to other examples, the method is characterized by a lower rate of side effects associated with intrathecal administration of cells in comparison to a corresponding method comprising intrathecal administering a therapeutic cell suspension comprising more than $2\times10^7$ cells/ml at a rate higher than 2 ml/min. According to yet another example, the side effects are selected from the group comprising of: back pain, pain in lower limbs, cell clumping, thickening or mild enhancement of cauda equina nerve roots near the injection site, and any combinations thereof. According to some embodiments, cell clumping comprises cell clumping adjacent to the nerves near the injection site. According to some embodiments, cell clumping comprises cell clumping adjacent to the nerve roots of the cauda equina near the injection site. According to a more specific example, the therapeutic cell suspension comprises of a plurality of cells selected from the group comprising of: human stem cells, naïve (undifferentiated) adult stem cells, progenitor cells, differentiated cells derived from embryonic or adult stem cells, induced pluripotent stem cells, and combinations thereof. According to yet another example, the cells are the human stem cells. According to a more specific example, the human stem cells are derived from lamina propria of the oral mucosa. According to a more specific example, the cells are derived from the lining and masticatory oral mucosa. According to yet another example, the cells are characterized by simultaneously expressing the following markers: Oct-4, SSEA4, Nanog, Sox2, CD29, CD 73, CD90, CD105, and CD166. According to a more specific example, are characterized by simultaneously expressing the following markers: KLF4, c-MYC, and nestin, and wherein the cells are negative for CD45 and CD31.

According to another aspect, the present invention provides a therapeutic cell suspension for use in a method of treatment of a neurological disease or disorder in a subject in need thereof wherein the method comprises intrathecally administering of from 5 to 40 ml of the therapeutic cell suspension at a rate of from 0.1 to 2 ml/min and wherein (a) the amount of the administered cells is from $1\times10^6$ to $1\times10^9$; (b) the concentration of cells in the therapeutic cell suspension is from $1\times10^5$ to $2\times10^7$ cells/ml; or (c) both (a) and (b). In some examples, the method comprises intrathecally administering of from 5 to 35 ml of the therapeutic cell suspension at a rate of from 0.1 to 2 ml/min. In some examples, the method comprises intrathecally administering of from 5 to 30 ml of the therapeutic cell suspension at a rate of from 0.1 to 2 ml/min. In some examples, the method comprises intrathecally administering of from 5 to 25 ml of the therapeutic cell suspension at a rate of from 0.1 to 2 ml/min. All examples and embodiments related to a method of treatment of a neurological disease or disorder are contemplated in the aspect.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

The present invention provides a method of intrathecally administering a therapeutic cell suspension to a patient in need thereof suffering from a neurological disease or disorder. It was unexpectedly found that the slow administration rate and/or the relatively low concentration of cells optionally together with the Trendelenburg position allow to overcome previously reported side effects associated with intrathecal administration such as back pain, pain in lower limbs or those shown as lumbar MRI abnormalities such as cell clumping adjacent to the nerve roots near the injection site e.g. nerve roots of the cauda equina near the injection site, thickening or mild enhancement of cauda equina nerve roots near the injection site suggesting accumulation of cells in the injected area. Cell clumping might be associated with adverse events of considerable intensity and duration in addition to reduced therapeutic efficacy. Other reported side effects associated with intrathecal cell administration at a relatively fast rate and high concentration, included post-operative back pain of considerable intensity and duration with referral pain in the lower limbs. Without being bound to any particular theory it is assumed that the method of administration facilitates the dispersion of the cells within the cerebrospinal fluid (CSF) and their movement in a cranial direction. The provided mode of administration thereby allows for dispersing cells cranially, and their attachment to the surface of the arachnoid mater and pia mater as close as possible to the brain and along the length of the spinal cord. Subsequently, a higher number of cells reach its target and consequently enhance the desired therapeutic effect. The present invention provides methods for treating neurological diseases treatable by intrathecal administration of a therapeutic cell suspension implementing slow administration of the cell suspension to a patient in need thereof suffering from a neurological disease or disorder.

The present invention provides a method of administration with the following advantages:
(i) Locating the therapeutic cells as close as possible to the affected tissues within the brain or spinal cord.
(ii) Higher spreading of the cells allows for higher secreting surface and thereby the secretion of higher amounts of trophic factors.
(iii) Preventing cell accumulation in the administration area which is at the far (caudal) end of the CNS.
(iv) The use of higher concentrations and consequently higher doses of therapeutic cells with minimal side effects.

According to one aspect, the present invention provides a method for treating a neurological disease or disorder in a subject in need thereof comprising intrathecally administering from 5 to 40 ml of a therapeutic cell suspension at a rate of from 0.1 to 2 ml/min, wherein the amount of the administered cells is from $1\times10^6$ to $5\times10^8$ and/or wherein the concentration of cells in the therapeutic cell suspension is from $0.5\times10^5$ to $2\times10^7$ cells/ml. In some embodiments, the method comprises administering from 5 to 35 ml of the therapeutic cell suspension. In some embodiments, the method comprises administering from 5 to 30 ml of the therapeutic cell suspension. In some embodiments, the method comprises administering from 5 to 25 ml of the therapeutic cell suspension. In some embodiments, the method comprises administering from 5 to 20 ml of the therapeutic cell suspension. In some embodiments, the method comprises administering from 5 to 15 ml of the therapeutic cell suspension. In some embodiments, the method comprises administering from 10 to 25 ml of the therapeutic cell suspension. In some embodiments, the method comprises administering from 15 to 25 ml of the therapeutic cell suspension. In some embodiments, the method comprises administering from 10 to 20 ml of the therapeutic cell suspension. In some embodiments, the concentration of cells in the therapeutic cell suspension is from $1\times10^5$ to $2\times10^7$ cells/ml. In some embodiments, the concentration of cells in the therapeutic cell suspension is from $0.5\times10^6$ to $2\times10^7$ cells/ml. In some embodiments, the concentration of cells in the therapeutic cell suspension is from $1\times10^6$ to $2\times10^7$ cells/ml.

According to some embodiments, the present invention provides a method for treating a neurological disease or disorder in a subject in need thereof comprising intrathecally administering from 5 to 40 ml of a therapeutic cell suspension at a rate of from 0.1 to 2 ml/min, wherein the amount of the administered cells is from $1\times10^6$ to $5\times10^8$. According to other embodiments, the present invention provides a method for treating a neurological disease or disorder in a subject in need thereof comprising intrathecally administering from 5 to 40 ml of a therapeutic cell suspension at a rate of from 0.1 to 2 ml/min, wherein the concentration of cells in the therapeutic cell suspension is from $1\times10^5$ to $2\times10^7$ cells/ml. According to some embodiments, the method comprises performing a spinal puncture. According to some embodiments, the method comprises performing a lumbar puncture. As used herein, the term "lumbar puncture" refers to a spinal puncture between any two vertebrae of the spine. Therefore, according to one embodiment, the present invention provides a method for treating a neurological disease or disorder in a subject in need thereof comprising the steps of:
(i) performing a lumbar puncture; and
(ii) intrathecally administering from 5 to 40 ml of a therapeutic cell suspension at a rate of from 0.1 to 2 ml/min,
wherein the amount of the administered cells is from $1\times10^6$ to $5\times10^8$.

According to other embodiments, the present invention provides a method for treating a neurological disease or disorder in a subject in need thereof comprising the steps of:
(i) performing a lumbar puncture; and
(ii) intrathecally administering from 5 to 40 ml of a therapeutic cell suspension at a rate of from 0.1 to 2 ml/min,
wherein the concentration of cells in the therapeutic cell suspension is from $10^5$ to $2\times10^7$ cells/ml.

According to some embodiments, the lumbar puncture is performed using a spinal needle.

According to any one of the above embodiments, the method further comprises drawing a volume from 5 to 40 ml or from 5 to 35 ml of cerebrospinal fluid (CSF) at step (i). According to any one of the above embodiments, the method further comprises drawing a volume from 5 to 30 ml or from 5 to 25 ml of cerebrospinal fluid (CSF) at step (i). According to any one of the above embodiments, the method further comprises drawing a volume from 10 to 40 ml or from 10 to 30 ml of cerebrospinal fluid (CSF) at step (i). According to any one of the above embodiments, the method further comprises drawing a volume from 15 to 30 ml or from 10 to 20 ml of cerebrospinal fluid (CSF) at step (i). According to some embodiments, the volume of the administered therapeutic cell suspension is equal to or up to ±5 ml of the volume of CSF drawn in step (i). According to some embodiments, the administration and the drawing of the CSF are performed via the same puncture location. According to other embodiments, the administration and the drawing of the CSF are performed via the different puncture locations.

According to some embodiments, the present invention provides a method for treating a neurological disease or disorder in a subject in need thereof comprising the steps of:
(i) performing a lumbar puncture and drawing a volume from 5 to 30 ml of cerebrospinal fluid (CSF); and
(ii) intrathecally administering a therapeutic cell suspension at a rate of from 0.1 to 2 ml/min,
wherein the volume of the administered therapeutic cell suspension is equal to or up to ±5 ml the volume of CSF drawn in step (i). According to one embodiment, the amount of the administered cells is from $1\times10^6$ to $5\times10^8$. Thus, according to some embodiments, the present invention provides a method for treating a neurological disease or disorder in a subject in need thereof comprising the steps of:
(i) performing a lumbar puncture and drawing a volume from 5 to 30 ml of cerebrospinal fluid (CSF); and
(ii) intrathecally administering a therapeutic cell suspension at a rate of from 0.1 to 2 ml/min,
wherein the volume of the administered therapeutic cell suspension is equal to or up to ±5 ml the volume of CSF drawn in step (i) and the amount of the administered cells is from $1\times10^6$ to $5\times10^8$. In some embodiments, the method comprises drawing and/or intrathecally administering from 5 to 40 ml of CNS and/or therapeutic cell suspension. In some embodiments, the method comprises drawing and/or intrathecally administering from 5 to 25 ml of CNS and/or therapeutic cell suspension. In some embodiments, the method comprises drawing and/or intrathecally administering from 10 to 25 of CNS and/or therapeutic cell suspension. In some embodiments, the method comprises drawing and/or intrathecally administering from 10 to 20 of CNS and/or therapeutic cell suspension. According to some embodiments, the present invention provides a method for treating a neurological disease or disorder in a subject in need thereof comprising the steps of:
(i) performing a lumbar puncture and drawing a volume from 5 to 30 ml of cerebrospinal fluid (CSF); and
(ii) intrathecally administering a therapeutic cell suspension at a rate of from 0.1 to 2 ml/min,
wherein the volume of the administered therapeutic cell suspension is equal to or up to ±5 ml the volume of CSF drawn in step (i) and the concentration of cells in the therapeutic cell suspension is from $1\times10^6$ to $2\times10^7$ cells/ml.

According to some embodiments, the neurological disease or disorder is a neurodegenerative disease or disorder. The terms "neurological disease or disorder" and "neural disease or disorder" may be used interchangeably. Typically, the term "neural" refers to nerves or groups of nerves. According to some embodiments, neurodegenerative disease or disorder is selected from the group comprising of: a disease of basal ganglia and brain stem, a disease affecting the cerebral cortex, a spinocerebellar degeneration, a degenerative disease affecting motor neurons, or combinations thereof.

In some embodiments, the neurodegenerative disease is a disease of a basal ganglia and brain stem. According to some embodiments, the disease is Multiple System Atrophy. According to another embodiment, the disease is Parkinsonism. According to another embodiment, the disease is Idiopathic Parkinson's Disease. According to another embodiment, the disease is Progressive Supranuclear Palsy. According to another embodiment, the disease is Corticobasal Degeneration. According to another embodiment, the disease is Striatonigral Degeneration. According to another embodiment, the disease is Shy-Drager Syndrome. According to another embodiment, the disease is Olivopontocerebellar Atrophy. According to another embodiment, the disease is Huntington's Disease. According to some embodiments, the neurodegenerative disease is Multiple System Atrophy. According to some embodiments, the neurological disease or disorder is selected from the group comprising of trauma to central nervous system (CNS), brain trauma, trauma to the spinal cord, trauma to the spinal ganglions, and a chronic disease affecting the central nervous system. According to some embodiments, the chronic disease affecting the central nervous system is selected from diabetes, lupus, post-atherosclerotic stroke and post-hemorrhagic stroke caused by intervertebral disc pathologies. According to some embodiments, the present invention provides a method for treating Multiple System Atrophy in a subject in need thereof comprising intrathecally administering from 5 to 25 ml of a therapeutic cell suspension at a rate of from 0.1 to 2 ml/min, wherein the amount of the administered cells is from $1\times10^6$ to $5\times10^8$ and/or wherein the concentration of cells in the therapeutic cell suspension is from $0.5\times10^6$ to $2\times10^7$ cells/ml.

In some embodiments, the neurodegenerative disease is a disease affecting the cerebral cortex. According to some embodiments, the disease is Alzheimer's Disease. According to another embodiment, the disease is Pick Disease. In some embodiments, the neurodegenerative disorder is a Spinocerebellar degeneration. According to some embodiments, the disorder is Spinocerebellar Ataxias. According to another embodiment, the disorder is Friedreich Ataxia. According to another embodiment, the disorder is Ataxia-Telangiectasia.

In some embodiments, the neurodegenerative disease is a degenerative disease affecting motor neurons. According to some embodiments, the disease is Amyotrophic Lateral Sclerosis. According to another embodiment, the disease is Bulbospinal Atrophy. According to some embodiments, the disease is Spinal Muscular Atrophy.

The term "treating" a condition or patient refers to taking steps to obtain beneficial or desired results, including clinical results. Beneficial or desired clinical results include, but are not limited to, ameliorating, abrogating, substantially inhibiting, slowing or reversing the progression of a disease, condition or disorder, substantially ameliorating or alleviating clinical or esthetical symptoms of a condition, substantially preventing the appearance of clinical or esthetical symptoms of a disease, condition, or disorder, and protecting from harmful or annoying symptoms. Treating further refers to accomplishing one or more of the following: (a) reducing the severity of the disorder; (b) limiting the development of symptoms characteristic of the disorder(s) being treated; (c) limiting worsening of symptoms characteristic of the disorder(s) being treated; (d) limiting recurrence of the disorder(s) in patients that have previously had the disorder(s); and/or (e) limiting recurrence of symptoms in patients that were previously asymptomatic for the disorder(s). The term "treatment" as used herein refers to both therapeutic treatment and prophylactic or preventative measures. Those in need of treatment include those already with the disorder as well as those in which the disorder is to be prevented.

The composition of the present invention may be administered by any known method into the central neural system. The term "administering" or "administration of" a substance, a compound or an agent to a subject can be carried out using one of a variety of methods known to those skilled in the art. According to some embodiments, the administration is intrathecal administration. The term "intrathecal administration" or "intrathecal injection" refers to an injection into the spinal canal (intrathecal space surrounding the spinal cord). Various techniques may be used including, without limitation, lumbar puncture or lateral cerebroventricular injection through a borehole or cisternal or the like. In some embodiments, "intrathecal administration" or "intrathecal delivery" according to the present invention refers to IT administration or delivery via the lumbar area or region, i.e., lumbar IT administration or delivery. In some embodiments, the term intrathecal administration refers to administration into the subarachnoid space.

A "therapeutically effective amount" of a drug or agent is an amount of a drug or an agent that, when administered to a subject will have the intended therapeutic effect. The full therapeutic effect does not necessarily occur by the administration of one dose and may occur only after the administration of a series of doses. Thus, a therapeutically effective amount may be administered in one or more administrations. The precise effective amount needed for a subject will depend upon, for example, the subject's size, health and age, the nature and extent of the cognitive impairment, and the therapeutics or combination of therapeutics selected for administration, and the mode of administration. The skilled person can readily determine the effective amount for a given situation by routine experimentation.

In some examples, the present invention provides a method for intrathecally administering a therapeutic cell suspension to a subject in need thereof comprising the steps of:
(i) performing a lumbar puncture and drawing a volume of from 5 to 40 ml of cerebrospinal fluid (CSF); and (ii) intrathecally administering a therapeutic cell suspension at a rate of from 0.1 to 2 ml/min
wherein the volume of the administered therapeutic cell suspension is equal to or up to ±5 ml the volume of CSF drawn in step (i), and wherein the amount of the administered cells is from $1\times10^6$ to $5\times10^8$.

According to any one of the above aspects and embodiments, step (i) comprises drawing from 5 to 35 ml of CSF. According to some embodiments, step (i) comprises drawing from 5 to 30 ml of CSF. According to some embodiments, step (i) comprises drawing from 5 to 25 ml of CSF. According to some embodiments, step (i) comprises drawing from 5 to 20 ml of CSF. According to some embodiments, step (i) comprises drawing from 10 to 20 ml of CSF. According to some embodiments, step (i) comprises drawing from 10 to 25 ml of CSF. According to some embodiments, step (i) comprises drawing from 10 to 30 ml of CSF. According to some embodiments, step (i) comprises drawing from 8 to 12 ml of CSF. According to some embodiments, step (i) comprises drawing from 12.5 to 17.5 ml of CSF. According to some embodiments, step (i) comprises drawing about 15 ml of CSF.

According to any one of the above embodiments, the volume of the therapeutic cell suspension administered in step (ii) equals to the volume of CSF drawn in step (i). According to any one of the above embodiments, the volume of the therapeutic cell suspension administered in step (ii) is ±1 to 5 ml of the volume of CSF drawn in step (i). According to any one of the above embodiments, the volume of the therapeutic cell suspension administered in step (ii) is ±1 ml, or ±2 ml, or ±3 ml, or ±4 ml, or ±5 ml of the volume of CSF drawn in step (i).

According to any one of the above aspects and embodiments, the volume of the therapeutic cell suspension administered in step (ii) is from 5 to 40 ml. According to any one of the above aspects and embodiments, the volume of the therapeutic cell suspension administered in step (ii) is from 5 to 35 ml. According to any one of the above aspects and embodiments, the volume of the therapeutic cell suspension administered in step (ii) is from 5 to 30 ml. According to any one of the above aspects and embodiments, the volume of the therapeutic cell suspension administered in step (ii) is from 5 to 25 ml. According to any one of the above aspects and embodiments, the volume of the therapeutic cell suspension administered in step (ii) is from 5 to 20 ml. According to any one of the above aspects and embodiments, the volume of the therapeutic cell suspension administered in step (ii) is from 10 to 20 ml. According to any one of the above aspects and embodiments, the volume of the therapeutic cell suspension administered in step (ii) is from 12.5 to 17.5 ml. According to any one of the above aspects and embodiments, the volume of the therapeutic cell suspension administered in step (ii) is about 15 ml.

According to any one of the above aspects and embodiments, the rate of administration of the therapeutic cell suspension is from 0.1 to 1.5 ml/min. According to any one of the above aspects and embodiments, the rate of administration of the therapeutic cell suspension is from 0.5 to 1.5 ml/min. According to some embodiments, the rate of administration of the therapeutic cell suspension is from 0.6 to 1.3 ml/min. According to some embodiments, the rate of administration of the therapeutic cell suspension is from 0.8 to 1.2 ml/min. According to some embodiments, the rate of administration of the therapeutic cell suspension is about 1 ml/min. According to some embodiments, the administration of therapeutic cell suspension is performed at step (ii). According to some embodiments, the rate of administration of the therapeutic cell suspension at step (ii) is from 0.1 to 1.5 ml/min, from 0.5 to 1.5 ml/min, from 0.6 to 1.3 ml/min, from 0.8 to 1.2 ml/min or about 1 ml/min.

As used herein the term "therapeutic cell suspension" refers to a suspension of cells in a pharmaceutically acceptable carrier and is intended for therapeutic purposes, typically administered through injection or infusion into a patient's body. This suspension contains a specific population of cells that possess therapeutic properties, such as stem cells, or other specialized cell types. These cells are isolated, processed and suspended in a suitable solution or medium to maintain their viability and functionality.

According to any one of the above aspects and embodiments, the therapeutic cell suspension comprises cells selected from the group comprising of: naïve (undifferentiated) adult stem cells, progenitor cells, differentiated cells derived from embryonic or adult stem cells, induced pluripotent stem cells (Yamanaka), and combinations thereof. According to some embodiments the therapeutic cell suspension comprises of naïve (undifferentiated) adult stem cells. According to other embodiments, induced pluripotent stem cells encompass also the derivatives of the induced pluripotent stem cells. According to other embodiments, the therapeutic cell suspension comprises progenitor cells. According to other embodiments, the therapeutic cell suspension comprises neural progenitor cells. According to other embodiments the therapeutic cell suspension comprises cells engineered to express neurotrophic factors. According to other embodiments the therapeutic cell suspension comprises differentiated cells derived from embryonic or adult stem cells. According to other embodiments the therapeutic cell suspension comprises of induced pluripotent stem cells.

In some embodiments, the cells are human stem cells. According to some embodiments, the therapeutic cell suspension comprises human oral mucosa stem cells. According to some embodiments the therapeutic cell suspension comprises human stem cells derived from the lamina propria of the oral mucosa (hOMSC). According to some embodiments, the cells are derived from the lining and masticatory oral mucosa. In some embodiments, the cells are derived from the oral mucosa of the gingiva. According to some embodiments, the cells are characterized by simultaneously expressing the following markers: OCT-4, SSEA4, NANOG, SOX2, CD29, CD 73, CD90, CD105, and CD166. According to some embodiments, the cells are characterized by simultaneously expressing the following markers KLF4, c-MYC, and nestin and being negative for CD45 and CD31. According to some embodiments, the cells are characterized by simultaneously expressing the following markers: OCT-4, SSEA4, NANOG, SOX2, KLF4, c-MYC, nestin, CD29, CD 73, CD90, CD105, and CD166; the cells are negative for CD45 and CD31. According to some embodiments, the cells are isolated cells. According to some embodiments, the cells are pluripotent or multipotent stem cells.

The term "oral mucosa" refers to the mucosal lining the oral cavity, namely: the cheeks and the alveolar ridge including the gingiva and the palate, the tongue, the floor of the mouth and the oral part of the lips. Oral mucosa is the mucosal lining the oral cavity, namely: the cheeks and the alveolar ridge including the gingiva and the palate, the tongue, the floor of the mouth and the oral part of the lips. Oral mucosa consists of an epithelial tissue of ectodermal origin and the lamina propria (LP) which is a connective tissue of ectomesenchymal origin. Similarly, to the ectomesenchymal origin of connective tissues in the oral cavity, cells of the oral mucosa lamina propria (OMLP) originate from the embryonic ectodermal neural crest.

The term "hOMSC" refers to human stem cells derived from the lamina propria of the oral mucosa. According to some embodiments, the hOMSC are characterized by simultaneously expressing the following markers KLF4, c-MYC, and nestin and being negative for CD45 and CD31. According to some embodiments, hOMSC are characterized by simultaneously expressing the following markers: OCT-4, SSEA4, NANOG, SOX2, KLF4, c-MYC, nestin, CD29, CD 73, CD90, CD105, and CD166; the cells being negative for CD45 and CD31.

The term "Stem cells" (SC) refers to undifferentiated cells, which can give rise to a succession of mature functional cells. Differentiated stem cells or stem cell population according to the present invention refer to partially or fully differentiated stem cells or naïve stem cell population.

The term "Embryonic stem (ES) cells" refers to cells derived from the inner cell mass of the embryonic blastocysts that are pluripotent, thus possessing the capability of developing into any organ or tissue type or, at least potentially, into a complete embryo.

The term "Adult stem cells" refers to post-natal stem cells derived from tissues, organs or blood of an organism after its birth.

The term "Pluripotent stem cells" refers to stem cells capable of generating the three embryonic cell layers and their derivatives cell lineages and tissues;

The term "Multipotent stem cells" refers to stem cells capable of forming multiple cell lineages that constitute an entire tissue or organ.

According to some embodiments, the method comprises administering from $1\times10^7$ to $5\times10^8$ of cells. According to some embodiments, the method comprises administering from $15\times10^6$ to $500\times10^6$ of cells. According to some embodiments, the method comprises administering from $20\times10^6$ to $150\times10^6$ of cells. According to some embodiments, the method comprises administering from $30\times10^6$ to $100\times10^6$ of cells. According to some embodiments, the method comprises administering from $30\times10^6$ to $80\times10^6$ of cells. According to some embodiments, the method comprises administering about $37.5\times10^6$ cells. According to some embodiments, the method comprises administering about $75\times10^6$ cells. According to some embodiments, the cells are hOMSC.

In some embodiments, the therapeutic cell suspension comprises from $0.1\times10^5$ to $5\times10^8$ cells/ml. In some embodiments, the therapeutic cell suspension comprises from $0.5\times10^5$ to $5\times10^8$ cells/ml. In some embodiments, the therapeutic cell suspension comprises from $1\times10^5$ to $5\times10^8$ cells/ml. In some embodiments, the therapeutic cell suspension comprises from $0.1\times10^6$ to $5\times10^8$ cells/ml. In some embodiments, the therapeutic cell suspension comprises from $0.5\times10^6$ to $5\times10^8$ cells/ml. In some embodiments, the therapeutic cell suspension comprises from $1\times10^5$ to $1\times10^7$ cells/ml. In some embodiments, the therapeutic cell suspension comprises from $5\times10^5$ to $5\times10^6$ cells/ml. In some embodiments, the therapeutic cell suspension comprises from $1\times10^6$ to $1\times10^7$ cells/ml. In some embodiments, the therapeutic cell suspension comprises from $0.1\times10^6$ to $2\times10^7$ cells/ml. In some embodiments, the therapeutic cell suspension comprises from $0.5\times10^6$ to $2\times10^7$ cells/ml. In some embodiments, the therapeutic cell suspension comprises from $1\times10^6$ to $2\times10^7$ cells/ml. In some embodiments, the therapeutic cell suspension comprises from $1\times10^6$ to $10\times10^6$ cells/ml. In some embodiments, the therapeutic cell suspension comprises from $1\times10^6$ to $7\times10^6$ cells/ml. In some embodiments, the therapeutic cell suspension comprises from $1\times10^6$ to $6\times10^6$ cells/ml. In some embodiments, the therapeutic cell suspension comprises from $1\times10^6$ to $5\times10^6$ cells/ml. In some embodiments, the therapeutic cell suspension comprises from $5\times10^5$ to $5\times10^6$ cells/ml. In some embodiments, the therapeutic cell suspension comprises from $2\times10^6$ to $5\times10^6$ cells/ml. In some embodiments, the therapeutic cell suspension comprises from $2.5\times10^6$ to $4\times10^6$ cells/ml. According to some embodiments, the cells are hOMSC.

According to some embodiments, the present invention provides a method for treating a neurological disease or disorder in a subject in need thereof comprising the steps of:
 (i) performing a lumbar puncture and drawing a volume from 5 to 40 ml of cerebrospinal fluid (CSF); and
 (ii) intrathecally administering a therapeutic cell suspension at a rate of from 0.1 to 1.5 ml/min,
 wherein the volume of the administered therapeutic cell suspension is equal to or up to ±5 ml the volume of CSF drawn in step, and wherein (a) the therapeutic cell suspension comprises from $1\times10^6$ to $5\times10^8$ cells, (b) the concentration of cells in the therapeutic cell suspension is from $1\times10^5$ to $2\times10^7$ cells/ml or (c) both (a) and (b). According to some embodiments, the method comprises drawing a volume from 5 to 35 or from 5 to 30 ml of cerebrospinal fluid (CSF). According to some embodiments, the method comprises drawing a volume from 5 to 25 of cerebrospinal fluid (CSF). According to some embodiments, the method comprises drawing a volume from 10 to 25 of cerebrospinal fluid (CSF). According to some embodiments, the method comprises drawing a volume from 10 to 20 of cerebrospinal fluid (CSF). According to some embodiments, the cells are hOMSC. According to one embodiment method comprises administering from $1\times10^6$ to $5\times10^8$ cells and the therapeutic cell suspension comprises from $0.5\times10^6$ to $2\times10^7$ cells/ml. According to one embodiment, the method comprises administering the therapeutic cell suspension comprising from $1\times10^6$ to $2\times10^7$ cells/ml.

According to some embodiments, the present invention provides a method for treating a neurodegenerative disease or disorder in a subject in need thereof comprising intrathecally administering from 5 to 25 ml of a therapeutic cell suspension comprising hOMSC at a rate of from 0.1 to 2 ml/min, wherein the amount of the administered cells is from $10\times10^6$ to $200\times10^6$ and/or the therapeutic cell suspension comprises from $1\times10^6$ to $2\times10^7$ cells/ml. According to some embodiments, the method comprises performing a lumbar puncture and drawing a volume from 5 to 25 ml of cerebrospinal fluid (CSF), wherein the volume of the administered therapeutic cell suspension is equal to or up to ±5 ml the volume of CSF drawn. According to some embodiments, the present invention provides a method for treating a neurodegenerative disease or disorder in a subject in need thereof comprising the steps of:
 (i) performing a lumbar puncture and drawing a volume from 5 to 25 ml of cerebrospinal fluid (CSF); and
 (ii) intrathecally administering a therapeutic cell suspension comprising hOMSC at a rate of from 0.1 to 2 ml/min,
wherein the volume of the administered therapeutic cell suspension is equal to or up to ±5 ml the volume of CSF drawn in step (i), and wherein the amount of the administered cells is from $10\times10^6$ to $200\times10^6$ and/or the therapeutic cell suspension comprises from $1\times10^6$ to $2\times10^7$ cells/ml. In some embodiments, the method comprises drawing from 10 to 20 ml of CSF. In one embodiment, the method comprises drawing about 15 ml of CSF. In one embodiment, the number of administered hOMSC is from $10 \times 10^6$/ml to $100 \times 10^6$/ml. In one embodiment, the concentration of hOMSC in the therapeutic cell suspension is from $1 \times 10^6$ to $15 \times 10^6$ cells. In one embodiment, the concentration of hOMSC in the therapeutic cell suspension is from $1 \times 10^6$ to $10 \times 10^6$ cells/ml. In one embodiment, the concentration of hOMSC in the therapeutic cell suspension is from $1 \times 10^6$/ml to $5 \times 10^6$/ml cells. According to some embodiments, the lumbar puncture is performed using a spinal needle.

According to some embodiments, the present invention provides a method for treating a neurodegenerative disease or disorder in a subject in need thereof comprising the steps of:
(i) performing a lumbar puncture using a spinal needle and drawing a volume of 15±5 ml of cerebrospinal fluid (CSF); and
(ii) intrathecally administering 15±5 ml of a therapeutic cell suspension comprising from $20 \times 10^6$ to $100 \times 10^6$ hOMSC at a rate of from 0.1 to 1.2 ml/min. According to some embodiments, the neurodegenerative disease is Multiple System Atrophy.

According to some embodiments, the present invention provides a method for treating a neurodegenerative disease or disorder in a subject in need thereof comprising the steps of:
(i) performing a lumbar puncture using a spinal needle and drawing a volume of 15±5 ml of cerebrospinal fluid (CSF); and
(ii) intrathecally administering 15±5 ml of a therapeutic cell suspension comprising from $1 \times 10^6$ to $5 \times 10^6$ hOMSC/ml at a rate of from 0.1 to 1.2 ml/min. According to some embodiments, the neurodegenerative disease is Multiple System Atrophy.

The described dosage refers to a dosage to an adult subject. The dosage of subjects belonging to other groups of subjects (e.g., children, toddlers, infants, newborns) may be adapted and calculated according to the ratio between the common range of the CSF in adults and the corresponding common range of the CSF in subjects of the group.

According to some embodiments, the therapeutic cell suspension comprises cells of autologous nature. According to other embodiments, the therapeutic cell suspension comprises cells of allogeneic nature.

According to some embodiments, the therapeutic cell suspension is administered via the spinal needle.

According to some embodiments, the therapeutic cell suspension is mixed during administration to prevent the clumping of cells. According to some embodiments, the mixing comprises rotating or tilting the device (e.g. a syringe) comprising the therapeutic cell suspension. According to one embodiment, the mixing is performed manually. In other embodiments, the mixing is performed by a designated automatic device.

According to any one of the above embodiments, the method further comprises placing the subject in Trendelenburg position.

According to any one of the aspects and embodiments of the application, the administration may be performed manually or by an automatic syringe pump/injector.

According to any one of the aspects and embodiments, the method according to the present invention is characterized by a lower rate of side effects associated with intrathecal administration of cells. According to some embodiments, the method according to the present invention is characterized by a lower rate of side effects associated with intrathecal administration of cells in comparison to a corresponding method comprising administering cells at a rate higher than 1.5 or higher than 2 ml/min. According to some embodiments, the method according to the present invention is characterized by a lower rate of side effects associated with intrathecal administration of cells in comparison to a corresponding method comprising intrathecal administering a therapeutic cell suspension comprising more than $2 \times 10^7$ cells/ml at a rate higher than 2 ml/min. The term "corresponding" refers to a method having the same steps and parameters except for the state one.

According to some embodiments, the side effects associated with intrathecal administration of cells are selected from the group comprising of back pain, pain in lower limbs, cell clumping, thickening or mild enhancement of the cauda equina nerve roots near the injection site, and any combinations thereof. According to some embodiments, cell clumping comprises cell clumping adjacent to the nerve roots of the cauda equina near the injection site. Therefore, according to some embodiments, the method of the present invention causes less of at least one of the following side effects: back pain, pain in lower limbs, cell clumping, thickening or mild enhancement of the cauda equina nerve roots near the injection site. According to one embodiment, the method described in this invention reduces the rate of occurrence of a back pain. According to another embodiment, the method described in this invention reduces the rate of occurrence of pain in lower limbs. According to another embodiment, the method described in this invention reduces the rate of occurrence of cell clumping adjacent to the nerve roots of the cauda equina near the injection site. According to another embodiment, the method described in this invention reduces the rate of occurrence of thickening of the cauda equina nerve roots near the injection site. According to another embodiment, the method described in this invention reduces the rate of occurrence of enhancement of the cauda equina nerve roots near the injection site as detected e.g., by MRI.

According to another aspect, the present invention provides a therapeutic cell suspension for use in a method of treatment of a neurological disease or disorder in a subject in need thereof wherein the method comprises intrathecally administering of from 5 to 40 ml of the therapeutic cell suspension at a rate of from 0.1 to 2 ml/min and wherein (a) the amount of the administered cells is from $1 \times 10^6$ to $5 \times 10^8$; (b) the concentration of cells in the therapeutic cell suspension is from $1 \times 10^5$ to $2 \times 10^7$ cells/ml; or (c) both (a) and (b). In some examples, the use comprises intrathecally administering from 5 to 35 ml of the therapeutic cell suspension. In some examples, the use comprises intrathecally administering from 5 to 30 ml of the therapeutic cell suspension. In some examples, the use comprises intrathecally administering from 5 to 25 ml of the therapeutic cell suspension. All terms, embodiments and definitions disclosed in any one of the above aspects apply and are encompassed herein as well. According to some embodiments, the present invention provides a therapeutic cell suspension for use in a method of treatment of a neurological disease or disorder in a subject in need thereof comprising intrathecally administering from 5 to 25 ml of the therapeutic cell suspension at a rate of from 0.1 to 2 ml/min, wherein the amount of the administered cells is from $1 \times 10^6$ to $5 \times 10^8$. According to some embodiments, the present invention provides a therapeutic cell suspension for use in a method of treatment of a neurological disease or disorder in a subject in need thereof comprising intrathecally administering from 5 to 40 ml of the therapeutic cell suspension at a rate of from 0.1 to 2 ml/min, wherein the concentration of cells in the therapeutic cell suspension is from $1 \times 10^5$ to $2 \times 10^7$ cells/ml. According to some embodiments, the subject is a subject from which a volume from 5 to 25 ml of cerebrospinal fluid (CSF) had been drawn.

According to some embodiments, the method comprises performing a lumbar puncture.

According to some embodiments, the present invention provides a therapeutic cell suspension for use in a method of treatment of a neurological disease or disorder in a subject in need thereof, wherein the method comprises
  (i) drawing a volume from 5 to 40 ml of cerebrospinal fluid (CSF); and
  (ii) intrathecally administering from 5 to 40 ml of a therapeutic cell suspension at a rate of from 0.1 to 2 ml/min,
  wherein (a) the amount of the administered cells is from $1\times10^6$ to $5\times10^8$; (b) the concentration of cells in the therapeutic cell suspension is from $1\times10^5$ to $2\times10^7$ cells/ml; or (c) both (a) and (b). According to some embodiments, the use comprises drawing from 5 to 35 ml of CSF in step (i). According to some embodiments, the use comprises drawing from 5 to 30 ml of CSF in step (i). According to some embodiments, the use comprises drawing from 5 to 25 ml of CSF in step (i). According to some embodiments, the use comprises intrathecally administering from 5 to 35 ml of CSF in step (ii). According to some embodiments, the use comprises intrathecally administering from 5 to 30 ml of CSF in step (ii). According to some embodiments, the use comprises intrathecally administering from 5 to 25 ml of CSF in step (ii). In some embodiments, the volume of the administered therapeutic cell suspension is equal to or up to ±5 ml of the volume of CSF drawn in step (i). According to some embodiments, the neurological disease or disorder is a neurodegenerative disease or disorder. According to some embodiments, neurodegenerative disease or disorder is selected from the group comprising of: a disease of basal ganglia and brain stem, a disease affecting the cerebral cortex, a spinocerebellar degeneration, a degenerative disease affecting motor neurons, or combinations thereof. In some embodiments, the neurodegenerative disease is a disease of a basal ganglia and brain stem. According to some embodiments, the disease is Multiple System Atrophy. According to another embodiment, the disease is Parkinsonism. According to another embodiment, the disease is Idiopathic Parkinson's Disease. According to another embodiment, the disease is Progressive Supranuclear Palsy. According to another embodiment, the disease is Corticobasal Degeneration. According to another embodiment, the disease is Striatonigral Degeneration. According to another embodiment, the disease is Shy-Drager Syndrome. According to another embodiment, the disease is Olivopontocerebellar Atrophy. According to another embodiment, the disease is Huntington's Disease. According to some embodiments, the neurodegenerative disease is Multiple System Atrophy.

According to any one of the above embodiments, the therapeutic cell suspension is formulated for intrathecal administration.

According to some embodiments, the therapeutic cell suspension comprises cells selected from naïve (undifferentiated) adult stem cells, progenitor cells, differentiated cells derived from embryonic or adult stem cells, induced pluripotent stem cells, and combinations thereof. According to some embodiments the therapeutic cell suspension comprises of naïve (undifferentiated) adult stem cells. In some embodiments the cells are human stem cells. According to some embodiments the therapeutic cell suspension comprises of human stem cells derived from the lamina propria of the oral mucosa (hOMSC). According to some embodiments, the cells are derived from the lining and masticatory oral mucosa. In some embodiments, the cells are derived from the oral mucosa of the gingiva. According to some embodiments, the cells are characterized by simultaneously expressing the following markers: OCT-4, SSEA4, NANOG, SOX2, CD29, CD 73, CD90, CD105, and CD166. According to some embodiments, the cells are characterized by simultaneously expressing the following markers KLF4, c-MYC and nestin, and being negative for CD45 and CD31. According to some embodiments, the cells are characterized by simultaneously expressing the following markers: OCT-4, SSEA4, NANOG, SOX2, KLF4, c-MYC, nestin, CD29, CD 73, CD90, CD105, and CD166; the cells are negative for CD45 and CD31. According to some embodiments, the cells are isolated cells. According to some embodiments, the cells are pluripotent or multipotent stem cells.

According to some embodiments, the use comprises drawing from 5 to 40 ml of CSF in step (i). According to some embodiments, the use comprises drawing from 5 to 35 ml of CSF in step (i). According to some embodiments, the use comprises drawing from 5 to 30 ml of CSF in step (i). According to some embodiments, the use comprises drawing from 5 to 25 ml of CSF in step (i). According to some embodiments, the use comprises drawing from 5 to 20 ml of CSF in step (i). According to some embodiments, the use comprises drawing from 10 to 20 ml of CSF in step (i). According to some embodiments, the use comprises drawing from 12.5 to 17.5 ml of CSF in step (i). According to some embodiments, the use comprises drawing about 15 ml of CSF in step (i).

According to any one of the above embodiments, the rate of administration of the therapeutic cell suspension is from 0.1 to 1.5 ml/min. According to some embodiments, the rate of administration of the therapeutic cell suspension is from 0.5 to 1.5 ml/min. According to some embodiments, the rate of administration of the therapeutic cell suspension is from 0.6 to 1.3 ml/min. According to some embodiments the rate of administration of the therapeutic cell suspension is from 0.8 to 1.2 ml/min. According to some embodiments the rate of administration of the therapeutic cell suspension is about 1 ml/min. According to some embodiments, the administration therapeutic cell suspension is performed at step (ii). According to some embodiments, the rate of administration of the therapeutic cell suspension at step (ii) is from 0.1 to 1.5 ml/min, from 0.5 to 1.5 ml/min, from 0.6 to 1.3 ml/min, from 0.8 to 1.2 ml/min or about 1 ml/min.

According to some embodiments, the use comprises administering from $1\times10^7$ to $1\times10^9$ of cells. In some embodiments, the therapeutic cell suspension comprises from $1\times10^6$ to $5\times10^8$ cells/ml. According to some embodiments, the use (the method) comprises administering from $15\times10^6$ to $500\times10^6$ of cells. According to some embodiments, the use comprises administering from $20\times10^6$ to $150\times10^6$ of cells. According to some embodiments, the use comprises administering from $30\times10^6$ to $100\times10^6$ of cells. According to some embodiments, the use comprises administering from $30\times10^6$ to $80\times10^6$ of cells. According to some embodiments, the use comprises administering about $37.5\times10^6$ cells. According to some embodiments, the use comprises administering about $75\times10^6$ cells. According to some embodiments, the cells are hOMSC.

In some embodiments, the therapeutic cell suspension comprises from $0.1\times10^5$ to $1\times10^7$ cells/ml. In some embodiments, the therapeutic cell suspension comprises from $0.5\times$ $10^5$ to $1\times10^7$ cells/ml. In some embodiments, the therapeutic cell suspension comprises from $1\times10^5$ to $1\times10^7$ cells/ml. In some embodiments, the therapeutic cell suspension comprises from $5\times10^5$ to $5\times10^6$ cells/ml. In some embodiments, the therapeutic cell suspension comprises from $1\times10^6$ to $1\times10^7$ cells/ml. In some embodiments, the therapeutic cell suspension comprises from $1\times10^6$ to $2\times10^7$ cells/ml. In some embodiments, the therapeutic cell suspension comprises from $1\times10^6$ to $10\times10^6$ cells/ml. In some embodiments, the therapeutic cell suspension comprises from $1\times10^6$ to $7\times10^6$ cells/ml. In some embodiments, the therapeutic cell suspension comprises from $1\times10^6$ to $6\times10^6$ cells/ml. In some embodiments, the therapeutic cell suspension comprises from $1\times10^6$ to $5\times10^6$ cells/ml. In some embodiments, the therapeutic cell suspension comprises from $2\times10^6$ to $5\times10^6$ cells/ml. In some embodiments, the therapeutic cell suspension comprises from $2.5\times10^6$ to $4\times10^6$ cells/ml. According to some embodiments, the cells are hOMSC.

According to any one of the above embodiments, the volume of the therapeutic cell suspension administered in step (ii) equals to the volume of CSF drawn in step (i). According to any one of the above embodiments, the volume of the therapeutic cell suspension administered in step (ii) is ±1 to 5 ml of the volume of CSF drawn in step (i). According to any one of the above embodiments, the volume of the therapeutic cell suspension administered in step (ii) is ±1 ml, or ±2 ml, or ±3 ml, or ±4 ml, or ±5 ml of the volume of CSF drawn in step (i).

According to any one of the above embodiments, the volume of the therapeutic cell suspension administered in step (ii) is from 5 to 40 ml. According to any one of the above embodiments, the volume of the therapeutic cell suspension administered in step (ii) is from 5 to 35 ml. According to any one of the above embodiments, the volume of the therapeutic cell suspension administered in step (ii) is from 5 to 35 ml. According to any one of the above embodiments, the volume of the therapeutic cell suspension administered in step (ii) is from 5 to 30 ml. According to some embodiments, the volume of the therapeutic cell suspension administered in step (ii) is from 5 to 25 ml. According to any one of the above aspects and embodiments, the volume of the therapeutic cell suspension administered in step (ii) is from 5 to 20 ml. According to any one of the above aspects and embodiments, the volume of the therapeutic cell suspension administered in step (ii) is from 10 to 20 ml. According to any one of the above aspects and embodiments, the volume of the therapeutic cell suspension administered in step (ii) is from 12.5 to 17.5 ml. According to any one of the above aspects and embodiments, the volume of the therapeutic cell suspension administered in step (ii) is about 15 ml.

According to some embodiments, the present invention provides a therapeutic cell suspension comprising hOMSC for use in a method of treatment of a neurodegenerative disease or disorder in a subject in need thereof comprising the steps of:
  (i) drawing a volume from 5 to 40 ml of cerebrospinal fluid (CSF); and
  (ii) intrathecally administering a therapeutic cell suspension comprising hOMSC at a rate of from 0.1 to 2 ml/min,
wherein the volume of the administered therapeutic cell suspension is equal to or up to ±5 ml the volume of CSF drawn in step (i), and wherein (a) the amount of the administered cells is from $10\times10^6$ to $200\times10^6$, (b) the therapeutic cell suspension comprises from $1\times10^5$ to $2\times10^7$ cells/ml, or (c) both (a) and (b). In some embodiments, the method comprises drawing from 10 to 20 ml of CSF. In one embodiment, the method comprises drawing from 15 to 30 ml of CSF. In one embodiment, the method comprises drawing from 15 to 25 ml of CSF. In one embodiment, the method comprises drawing about 15 ml of CSF. In one embodiment, the number of administered hOMSC is from $10\times10^6$ to $100\times10^6$. In one embodiment, the concentration of hOMSC in the therapeutic cell suspension is from $1\times10^6$ to $15\times10^6$ cells. In one embodiment, the concentration of hOMSC in the therapeutic cell suspension is from $1\times10^6$ to $10\times10^6$ cells. In one embodiment, the concentration of hOMSC in the therapeutic cell suspension is from $1\times10^6$ to $5\times10^6$ cells. The combination of several embodiments is contemplated as well. According to some embodiments, the neurodegenerative disease is Multiple System Atrophy.

According to some embodiments, the present invention provides a therapeutic cell suspension for use in a method of treatment of a neurodegenerative disease or disorder in a subject in need thereof the method comprises intrathecally administering 15±5 ml of a therapeutic cell suspension comprising from $20\times10^6$ to $100\times10^6$ hOMSC at a rate of from 0.1 to 1.2 ml/min. According to some embodiments, the method comprises drawing a volume of 15±5 ml of cerebrospinal fluid (CSF) before administering the therapeutic cell suspension. According to some embodiments, the neurodegenerative disease is Multiple System Atrophy.

According to some embodiments, the present invention provides a therapeutic cell suspension for use in a method of treatment of a neurodegenerative disease or disorder in a subject in need thereof the method comprises the steps of:
  (i) drawing a volume of 15±5 ml of cerebrospinal fluid (CSF); and
  (ii) intrathecally administering 15±5 ml of a therapeutic cell suspension comprising from $20\times10^6$ to $100\times10^6$ hOMSC at a rate of from 0.1 to 1.2 ml/min. According to some embodiments, the neurodegenerative disease is Multiple System Atrophy.

According to some embodiments, the present invention provides a therapeutic cell suspension for use in a method of treatment of a neurodegenerative disease or disorder in a subject in need thereof comprising the steps of:
  (i) drawing a volume of 15±5 ml of cerebrospinal fluid (CSF); and
  (ii) intrathecally administering 15±5 ml of a therapeutic cell suspension comprising from $1\times10^6$ to $7\times10^6$ hOMSC/ml at a rate of from 0.1 to 1.2 ml/min. According to some embodiments, the neurodegenerative disease is Multiple System Atrophy.

According to any one of the above embodiments, the method comprises a lumbar puncture using a spinal needle before drawing CSF or before administering the therapeutic cell suspension.

According to some embodiments, the use is characterized by a lower rate of side effects associated with intrathecal administration of cells in comparison to a corresponding method comprising intrathecal administering cells at a rate higher than 2 ml/min. According to some embodiments, the use is characterized by a lower rate of side effects associated with intrathecal administration of cells in comparison to a corresponding method comprising intrathecal administering of a therapeutic cell suspension comprising more than $2\times10^7$ cells/ml at a rate higher than 2 ml/min. According to some embodiments, the side effects are selected from the group comprising of back pain, pain in lower limbs, cell clumping, thickening or mild enhancement of cauda equina nerve roots near the injection site, and any combinations thereof. According to some embodiments, cell clumping comprises cell clumping adjacent to the nerves near the injection site. According to some embodiments, cell clumping comprises cell clumping adjacent to the nerve roots of the cauda equina near the injection site. According to some embodiments, the side effects associated with intrathecal administration of cells are selected from the group comprising of back pain, pain in lower limbs, cell clumping, thickening, or mild enhancement of the cauda equina nerve roots near the injection site, and any combinations thereof. Therefore, according to some embodiments, the method of the present invention causes less of at least one of the following side effects: back pain, pain in lower limbs, cell clumping, thickening or mild enhancement of the cauda equina nerve roots near the injection site. According to one embodiment, the method described in this invention reduces the rate of occurrence of back pain. According to another embodiment, the method described in this invention reduces the rate of occurrence of pain in lower limbs. According to another embodiment, the method described in this invention reduces the rate of occurrence of cell clumping adjacent to the nerve roots of the cauda equina near the injection. According to another embodiment, the method described in this invention reduces the rate of occurrence of thickening of the cauda equina nerve roots near the injection site. According to another embodiment, the method described in this invention reduces the rate of occurrence of enhancement of the cauda equina nerve roots near the injection site.

The following examples are intended to illustrate how to make and use the compounds and methods of this invention and are in no way to be construed as a limitation. Although the invention will now be described in conjunction with specific embodiments thereof, it is evident that many modifications and variations will be apparent to those skilled in the art. Accordingly, it is intended to embrace all such modifications and variations that fall within the spirit and broad scope of the appended claims.

EXAMPLES

Intrathecal therapeutic cell suspensions denoted hOMSC composition were prepared as follows.

Cryovials comprising about 2 ml of human oral mucosal stem cells (hOMSC), at a concentration of $10^7$-$10^8$ cells/mL frozen in a cryoprotecting composition were each thawed and dissolved in PlasmoLyle 148 (PL). The final volume of the therapeutic cell suspension was 15 ml and comprised 30-120×$10^6$ cells.

In other examples, the final volume of the therapeutic cell suspension is 5-20 ml and comprises 10-200×$10^6$ cells.

Storage

The DP bag is kept in a temperature-controlled environment (2-8° C.) until release test results are available. A total of 75±15×$10^6$ or 37.5±7.5×$10^6$ cells were administered in a single Intrathecal (IT) injection, following the clinical study protocol and the following instructions:

Administration of hOMSC:

The procedure is performed by a trained and experienced physician in reaching the intrathecal space by lumbar puncture (LP). The procedure is performed as follows:
1. Using sterile technique, a spinal needle is inserted in the subject's lumbar region through the skin and between two of the lower lumbar vertebrae (e.g., L3-L4, L4-L5; L5-S1). A 22G or 23G Sprotte Needle or equivalent is used for penetration of dura and collection of CSF.
2. After reaching the intrathecal space, the puncture needle is left in place until 10-20 ml of CSF are collected.
3. A 20 ml syringe containing 10-20 ml of hOMSC cell suspension (Product Syringe) is connected to the puncture needle by a catheter to facilitate administration. The cell suspension is injected at a rate of 0.5-1.5 ml/minute over 10-15 minutes. During the product administration, the syringe are inverted constantly to maintain cell suspension homogeneity and to ensure that there are no visible clumps prior to administration.
4. The puncture needle is left in place for additional 5 minutes and then removed.

Example 2. Formulation of Thawed Cells into Final Product

Cells, (human oral mucosa stem cells (hOMSC) were harvested and cryopreserved (cryo) with 5% DMSO at 9.42×$10^6$ viable cells/vial. Two parallel thawing protocol were tested.

Cells were each thawed into 20 ml of either PlasmaLyte 148 (PL) or in PL+5% human serum albumin (HAS), at 37° C., after which the vials were centrifuged. The cells were centrifuged and after draining the supernatant was washed with about 15 ml PL devoid of HSA to reach concentration of 3.3×$10^6$ cells/ml.

Administration of hOMSC:

The procedure was performed by a trained and experienced physician in reaching the intrathecal space by lumbar puncture (LP). The procedure was performed in four subjects suffering from multiple system atrophy as follows:
1. A lumbar puncture (LP) was performed by inserting a spinal needle in the subject's lumbar region through the skin and between two of the lower lumbar vertebrae (e.g., L3-L4, L4-L5; L5-S1). A 22G or 23G Sprotte Needle or equivalent is used for penetration of dura and collection of CSF.
2. After reaching the intrathecal space, the puncture needle is left in place until about 15 ml of CSF were collected.
3. A 20 ml syringe containing 15 ml of hOMSC cell suspension (Product Syringe) was connected to the puncture needle by a catheter to facilitate administration. The cell suspension was injected at a rate of about 1 ml/minute over 15 minutes. During the product administration, the syringe was inverted constantly to maintain cell suspension homogeneity and to ensure that there are no visible clumps prior to administration. The puncture needle is left in place for additional 5 minutes and then removed.

The patients did not report any side effects that are usually associated with IT administration of cell suspensions such as back pain, pain in lower limbs, cell clumping adjacent to the nerve root, thickening or mild enhancement of cauda equina nerve roots as observed e.g. by the MRI scans.

In another example, CSF is drawn from Cisterna *magna* and the suspension of hOMSC is administered via lumbar puncture.

Although the present invention has been described herein above by way of preferred embodiments thereof, it can be modified, without departing from the spirit and nature of the subject invention as defined in the appended claims

The invention claimed is:
1. A method for treating a neurological disease or disorder in a subject in need thereof comprising the steps of:
  (i) performing a lumbar puncture; and
  (ii) intrathecally administering from 5 to 40 ml of a therapeutic cell suspension at a rate of from 0.1 to 1.5 ml/min, wherein the therapeutic cell suspension comprises a plurality of human stem cells derived from lamina propria of the oral mucosa, and wherein the amount of the administered cells is from $1\times10^6$ to $5\times10^8$.

2. The method of claim 1, wherein the method further comprises drawing a volume from 5 to 40 ml of cerebrospinal fluid (CSF) at step (i) and wherein the volume of the administered therapeutic cell suspension is equal to or up to ±5 ml of the volume of CSF drawn in step (i).

3. The method according to claim 2, wherein the volume of the therapeutic cell suspension administered in step (ii) essentially equals to the volume of CSF drawn in step (i).

4. The method according to claim 1, wherein the neurological disease or disorder is a neurodegenerative disease.

5. The method of claim 4, wherein the neurodegenerative disease is selected from the group comprising of Multiple System Atrophy, Alzheimer's Disease, Pick Disease, Parkinsonism, Idiopathic Parkinson's Disease, Progressive Supranuclear Palsy, Corticobasal Degeneration, Striatonigral Degeneration, Shy-Drager Syndrome, Olivopontocerebellar Atrophy, Huntington Disease, Spinocerebellar Ataxias, Friedreich Ataxia, Ataxia-Telangiectasia, Amyotrophic Lateral Sclerosis, Bulbospinal Atrophy, Spinal Muscular Atrophy, and combinations thereof.

6. The method according to claim 4, wherein the neurological disease or disorder is selected from the group comprising of trauma to the brain and or to the spinal cord and or the spinal ganglions, chronic diseases that affect the central nervous system, diabetes, lupus, post-atherosclerotic stroke and post-hemorrhagic stroke caused by intervertebral disc pathologies.

7. The method according to claim 1, characterized by at least one of: (i) wherein the rate of administration of the therapeutic cell suspension at step (ii) is from 0.5 to 1.5 ml/min; (ii) the method comprises intrathecally administering from 5 to 30 ml of a therapeutic cell suspension; and (iii) the method further comprises drawing a volume from 5 to 30 ml of cerebrospinal fluid (CSF) at step (i) and wherein the volume of the administered therapeutic cell suspension is equal to or up to ±5 ml of the volume of CSF drawn in step (i).

8. The method according to claim 1, wherein the method comprises administering from $1\times10^7$ to $1\times10^8$ cells.

9. The method according to claim 1, wherein the concentration of cells in the therapeutic cell suspension is from $0.5\times10^5$ to $2\times10^7$ cells/ml.

10. The method according to claim 1, wherein the method is characterized by a lower rate of side effects associated with intrathecal administration of cells in comparison to a corresponding method comprising intrathecal administering cells at a rate higher than 2 ml/min or in comparison to a corresponding method comprising intrathecal administering a therapeutic cell suspension comprising more than $2\times10^7$ cells/ml at a rate higher than 2 ml/min.

11. The method according to claim 10, wherein the side effects are selected from the group comprising of back pain, pain in lower limbs, clumping of the administered cells adjacent to the nerve roots, thickening, or mild enhancement of cauda equina nerve roots near the injection site, and any combinations thereof.

12. The method according to claim 1, wherein the cells are derived from the lining and masticatory oral mucosa.

13. The method according to claim 12, wherein said cells are characterized by simultaneously expressing the following markers: Oct-4, SSEA4, Nanog, Sox2, CD29, CD 73, CD90, CD105, and CD166.

14. The method according to claim 1, wherein said cells are characterized by simultaneously expressing the following markers: KLF4, c-MYC and nestin, wherein the cells are negative for CD45 and CD31.

15. The method according to claim 1, wherein (i) the therapeutic cell suspension is administered via a spinal needle used for the lumbar puncture; (ii) the therapeutic cell suspension is mixed during the administration to prevent clumping of cells or (iii) both (i) and (ii).

16. The method according to claim 15, wherein the mixing comprises rotating or tilting the device comprising the therapeutic cell suspension.

17. A method for intrathecally administering a therapeutic cell suspension to a subject in need thereof comprising the steps of:
(i) performing a lumbar puncture using a spinal needle and drawing a volume of from 5 to 40 ml of cerebrospinal fluid (CSF); and
(ii) intrathecally administering a volume of a therapeutic cell suspension, being equal to or about ±5 ml of the volume of the CSF drawn in step (i), at a rate of from 0.1 to 1.5 ml/min,
wherein the therapeutic cell suspension comprises a plurality of human stem cells derived from lamina propria of the oral mucosa, and wherein the amount of the administered cells is from $1\times10^6$ to $5\times10^8$.

* * * * *